United States Patent
Collasius et al.

(10) Patent No.: US 6,315,902 B1
(45) Date of Patent: Nov. 13, 2001

(54) DEVICE FOR SELECTIVELY FILTERING UNDER REDUCED PRESSURE AND FOR VACUUM DRYING SAMPLE LIQUIDS OR DROPS OF SAMPLE LIQUIDS

(75) Inventors: Michael Collasius, Haan; Oliver-Guido Venschott, Münster, both of (DE)

(73) Assignee: Qiagen GmbH, Hilden (DE)

( * ) Notice: Subject to any disclaimer, the term of this patent is extended or adjusted under 35 U.S.C. 154(b) by 0 days.

(21) Appl. No.: 09/424,537

(22) PCT Filed: May 27, 1998

(86) PCT No.: PCT/EP98/03130

§ 371 Date: Nov. 24, 1999

§ 102(e) Date: Nov. 24, 1999

(87) PCT Pub. No.: WO98/53912

PCT Pub. Date: Dec. 3, 1998

(30) Foreign Application Priority Data

May 27, 1997 (DE) .............................. 197 22 021

(51) Int. Cl.[7] .............................. B01L 3/00; B01D 61/18; B01D 25/00; C12Q 1/68
(52) U.S. Cl. ................ 210/232; 210/416.1; 210/455; 210/470; 210/808; 422/101; 422/102; 422/104; 436/177
(58) Field of Search .................... 210/232, 416.1, 210/455, 770, 808; 455/101, 102, 104; 436/177

(56) References Cited

U.S. PATENT DOCUMENTS

| 4,427,415 | 1/1984 | Cleveland . |
| 5,306,420 | 4/1994 | Bisconte . |
| 5,645,723 | 7/1997 | Fijishiro et al. . |

FOREIGN PATENT DOCUMENTS

| 4107262A1 | 9/1992 | (DE) . |
| 0268946A2 | 6/1988 | (EP) . |
| 94/08716 | 4/1994 | (WO) . |

OTHER PUBLICATIONS

Patent Abstracts of Japan, vol. 097, no. 006, Jun. 30, 1997 & JP 09 047278 A.

*Primary Examiner*—David A. Reifsnyder
(74) *Attorney, Agent, or Firm*—Birch, Stewart, Kolasch & Birch, LLP

(57) ABSTRACT

A device for selectively filtering liquid samples in compartments comprising inlet and outlet openings of a carrier body under reduced pressure and vacuum drying drops of the sample liquid in the area of the outlet openings of the compartments. The device comprises a vacuum pump for producing two levels of subpressure, a suction conduit, and a chamber comprising an interior space limited by a top wall having an opening with an edge, a bottom wall, and lateral walls connecting the top and bottom walls. A lid or the carrier body with outlet openings directed towards the interior space of the chamber can be placed in a substantially gastight manner on the opening with an edge. One of the lateral walls is formed as an access wall which is opened and substantially gastightly sealed for introducing the carrier body into the interior space of the chamber.

13 Claims, 4 Drawing Sheets

Figure 1:
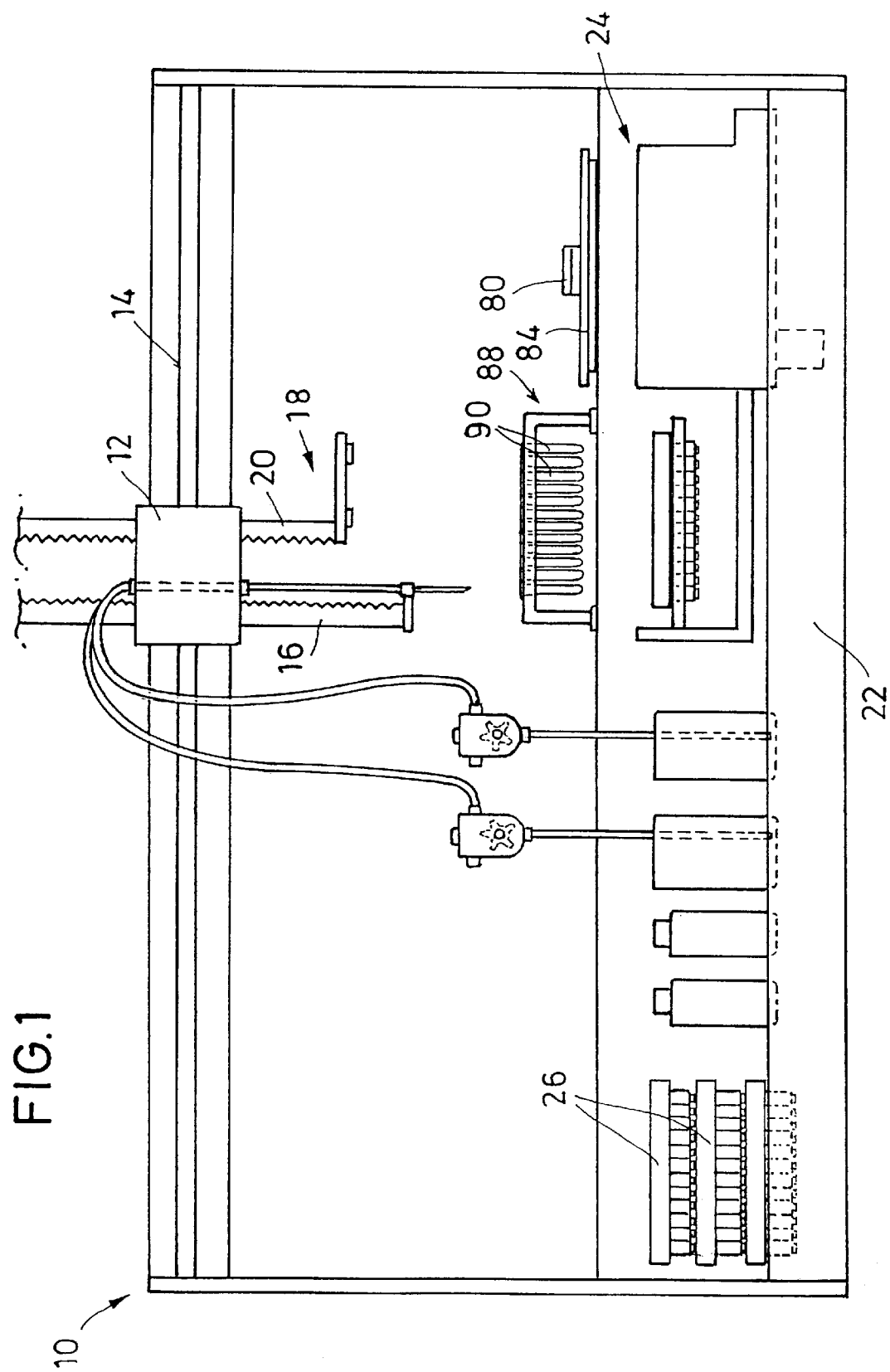

DEVICE FOR SELECTIVELY FILTERING UNDER REDUCED PRESSURE AND FOR VACUUM DRYING SAMPLE LIQUIDS OR DROPS OF SAMPLE LIQUIDS

This application is the national phase under 35 U.S.C. §371 of PCT International Application No. PCT/EP98/03130 which has an International filing date of May 27, 1998 which designated the United States of America.

The invention relates to a device for selectively filtering liquid samples in compartments comprising inlet and outlet openings of a carrier body under reduced pressure and vacuum drying drops present in the area of the outlet openings of the compartments. Furthermore, the invention relates to the uses of the device in the purifying of biopolymers, especially nucleic acids.

In molecular biology, in the analysis of samples, carrier bodies called microtitration plates are used comprising a plurality of compartments arranged two-dimensionally in lines and rows. These compartments are provided with inlet openings towards the upper side of the carrier body and comprise outlet openings on the lower side of the carrier body. In the compartments, there are filter bodies in the shape of frits or membranes provided to bond the substances of the liquid samples to be analyzed.

The sample liquids to be analyzed are introduced into the individual compartments of a carrier body (microtitration plates), if required after being processed. By applying a low pressure to the outlet openings of the compartments, it is provided that the sample liquids flow through the filter bodies of the compartments. In this process, the components to be analyzed and other components of the sample liquid get caught in the filter bodies. In order to obtain the components of interest of the liquid sample, the components which are not required have to be washed out of the filter bodies. For this purpose, wash buffers of various concentrations are pipetted into the compartments. By means of these wash buffers, a part of the components not of interest of the sample liquids is released form the filter bodies. By means of an elution buffer, the component of interest of the sample liquids is then washed out of the filter bodies. The pipetting and the flowing process of the wash buffers, the elution buffer and the sample liquids occur in a pipetting machine, which is computer controlled. These pipetting machines are provided with a vacuum chamber comprising an opening whereon the carrier bodies are substantially gastightly fitted to draw out the sample liquids or the wash buffers through the filter body. A device of the type described above is described in DE-A-41 07 262. In the filtration under reduced pressure, it always occurs that remaining liquids stay on the outlet openings of the compartments in the form of drops. Before the step of elution takes place, it has to be provided that these liquid drops have been removed. For the quantities to be analyzed occasionally are rather small so that a mixture with remaining liquid can lead to faulty results. What is more, components of the sample liquid which are not to be analyzed are present in the liquid drops, thus also adulterating the result of the analysis. In prior art, the carrier bodies, respectively microtitration plates, are dropped several times on a support having an absorbent material so that the liquid drops are virtually shaken off. However, this process cannot be integrated in the case of an automatic process, as in the case of a pipetting machine.

It is the object of the present invention to provide a device by means of which remaining liquid drops on the outlet opening of the compartments of the carrier bodies can be removed automatically and without manual interaction after a filtration process under reduced pressure has taken place.

To achieve this object, the invention proposes a device for selectively filtering liquid samples in compartments comprising inlet and outlet openings of a carrier body under reduced pressure and drying drops of the sample liquid present in the area of the outlet openings of the compartments, the device comprising:

- a chamber comprising an interior space limited by a top wall, a bottom wall and lateral walls connecting them,
- the top wall comprising an opening with an opening edge whereon a closing lid or the carrier body can selectively be put in a substantially gastight manner by means of outlet openings directed towards the interior space of the chamber,
- one of the lateral walls being formed as an access lateral wall which can be opened and closed substantially gastightly for introducing the carrier body into the interior space of the chamber, and
- the bottom wall comprising a drain for liquid exiting from the outlet openings of the compartments of the carrier body, and
- a vacuum pump with a suction conduit terminating in the interior space of the chamber for producing a first low pressure for drawing liquid samples through the outlet openings of the compartments with the carrier body being placed on the opening edge of the top wall and the access lateral wall of the chamber being closed and for producing a second low pressure higher than the first low pressure for drying drops of liquid samples still present on the outlet openings of the compartments with the carrier body being located in the interior space of the chamber and the lid being placed on the opening edge of the top wall as well as the access lateral wall of the chamber being closed.

The device according to the invention is provided with a low pressure chamber comprising a top wall, a bottom wall and lateral walls connecting them. One of the lateral walls is formed as an access lateral wall and can be opened and closed so that it is possible to introduce a compartment carrier body (subsequently called microtitration plate) via this lateral wall into the interior space of the chamber. Furthermore, the chamber comprises an opening in the top wall thereof being closable by means of a lid. As an alternative to the lid, a microtitration plate can also be placed onto the opening so that the chamber can then be used for filtering the sample liquid of the compartments under reduced pressure. The chamber comprises a drain in the bottom wall so that the flowing liquids can be drained.

The low pressure in the interior space of the chamber is produced by a vacuum pump connected to the interior space of the chamber by means of a suction conduit. By means of this vacuum pump, a first and a second low pressure can be produced alternatively in the interior space of the chamber. The first low pressure is required to draw in the sample liquid through the outlet opening of the compartments of the microtitration plate. Thus, the first low pressure is used for filtering under reduced pressure. The second low pressure higher than the first low pressure serves to dry sample liquid drops which might be adhering to the outlet openings of the microtitration plate at a vacuum. In the case of vacuum drying, the opening in the top wall of the chamber is closed by means of a lid, while the microtitration plate itself is located in the interior of the chamber. By lowering the pressure in the chamber, the evaporation point of the liquid drops is reduced, whereby they can be removed by evaporation.

By means of the device according to the invention, it is possible to use one and the same low pressure chamber both for filtering and for removing sample liquid drops. The manipulations to be executed on the chamber for this purpose, which are described above, can be put into practice without a problem by means of the gripping device of a pipetting machine so that manual interference is no longer necessary.

In an advantageous development of the invention, it is provided that the chamber comprises a support mounting for receiving the microtitration plate for putting it in the interior space of the chamber. Preferably, this support mounting is located on the interior side of the access lateral wall of the chamber directed towards the interior space, which wall is formed to be movable from the other walls of the chamber or towards them for this purpose. In this context, it is advantageous if the access lateral wall is provided with at least one cam element connected to the access lateral wall. The cam element can be moved by means of a driving device, whereby the access lateral wall is also moved. In this context, the cam element and the access lateral wall work in the manner of an automatic drawer which can be opened so far that the microtitration plate can be inserted from the top into the reception mounting by means of a gripping arm and can be taken out of the support mounting from the top, respectively.

In another advantageous development of the invention, it is further provided that the chamber comprises at least one heating element for heating the interior space. By means of this heating element, an appropriate temperature level can be set in the interior space of the chamber. The interior space of the chamber can also be heated during filtering under reduced pressure. In any case, heating the interior space is advantageous in the case of vacuum drying, as the conditions in the chamber can then be set more quickly such that liquid drops which might still be present are evaporated.

In order to simplify placing the lid or the microtitration plate on the opening edge of the top wall, it is suitable if the opening edge is provided with introduction surfaces extending angularly to the outside for centering the lid or the microtitration plate when it is put on. This has the advantage that the opening of the top wall can be closed automatically either by means of the lid or the microtitration plate, even if the positioning of the gripping arm is less accurate.

In order to be able to seal the interior space of the chamber against the environment without having moved the microtitration plate into the interior space of the chamber before and having closed the opening in the top wall by means of the lid, it is advantageous to insert a sealing body or a sealing mat consisting of a substantially gastight material and being placed on top of the inlet opening of the compartments of the microtitration plate, if it is located in the opening of the top wall. After a filtration under reduced pressure has taken place, the microtitration plate can remain in the opening of the top wall to for vacuum drying liquid drops which might be adhering to the outlet openings.

The device according to the invention preferably can be included into a pipetting apparatus comprising:
  a movable gripping device for gripping a carrier body comprising multiple compartments for receiving liquid samples, and
  a control means for controlling the gripping device.

The device according to the invention can especially be employed for isolating, separating and/or purifying of biopolymers, as is mentioned in the claims 14 to 18 and also described in EP-A-0 268 946; this document is included by reference in the disclosure of the instant application.

In particular the device according to the invention preferably can be used for separating, isolating and/or purifying biopolymers from mixtures containing the biopolymers. Most preferably, these biopolymers comprise peptides, proteins, nucleic acids, especially DNA and/or RNA, oligo- and/or polysaccharides. In particular, the DNA is a genomic or a plasmid DNA.

The device according to the invention can also be used for isolating a substance of interest, especially a biopolymer, from a sample comprising different substances and being located in a compartment having an inlet opening as well as an outlet opening and a porous matrix material arranged therebetween, to which the substances of the sample are immobilized by means of different affinities. The substance of interest in particular is a nucleic acid or a oligo- or polynucleotide. When using the device for the above purpose, the following steps are carried out:
  feeding a wash buffer into the inlet opening of the compartment for releasing those substances from the matrix material the affinity of which to the matrix material is smaller than the affinity by means of which the substance of interest is bound to the material,
  drawing the wash buffer and the solved substances through the matrix material by means of low pressure and out of the outlet opening of the compartment, by using the device according to the invention operated for filtering under reduced pressure,
  removing of residual material which might still be present on the outlet opening of the compartment, by using the device according to the invention operated for vacuum drying,
  and feeding an elution buffer into the inlet opening of the compartment for releasing substantially merely the substance of interest from the matrix material,
  drawing the elution buffer and the substance of interest by means of low pressure through the matrix material and out of the outlet opening of the compartment, by using the device according to the invention again operated for filtering under reduced pressure, while simultaneously filtering the elution buffer and the substance of interest exiting from the outlet opening into a compartment inserted into a support mounting of the access lateral wall of the chamber of the device according to the invention.

Figure 2:
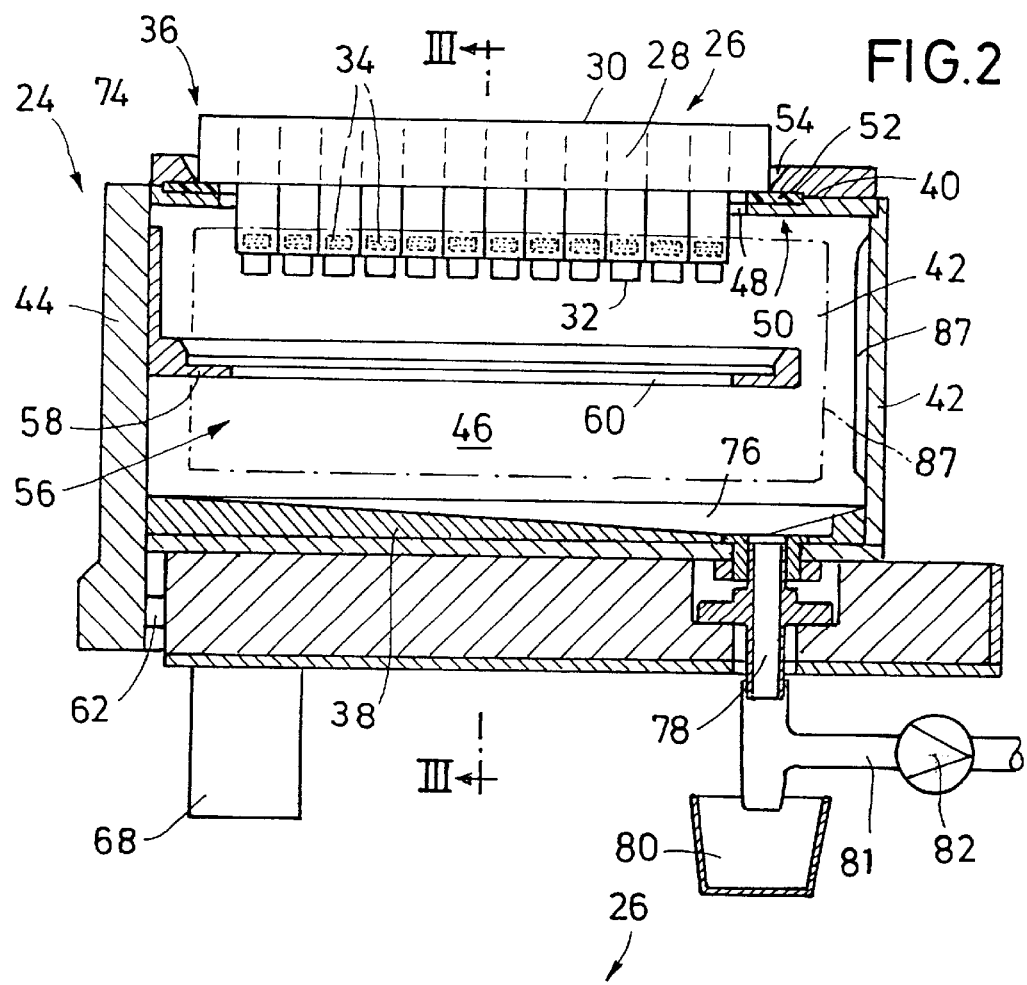
Figure 3:
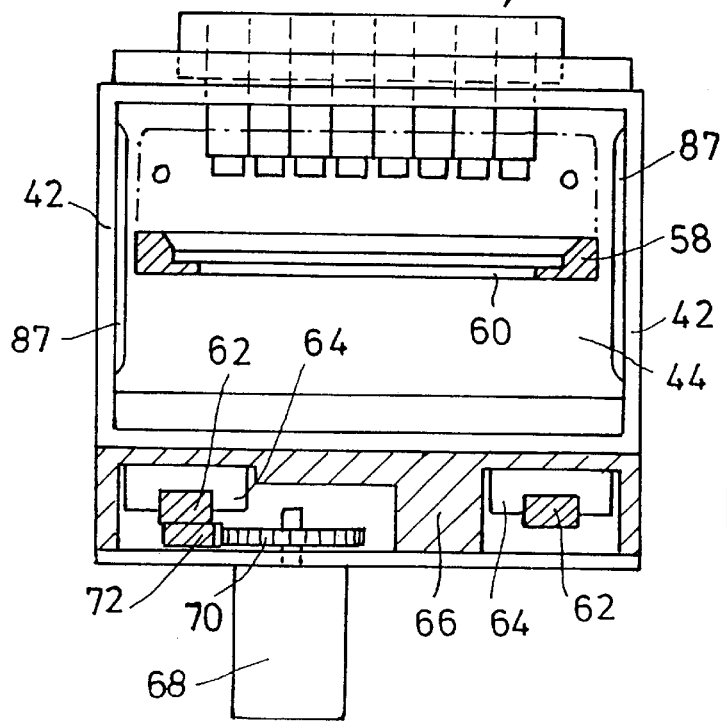
Figure 4:
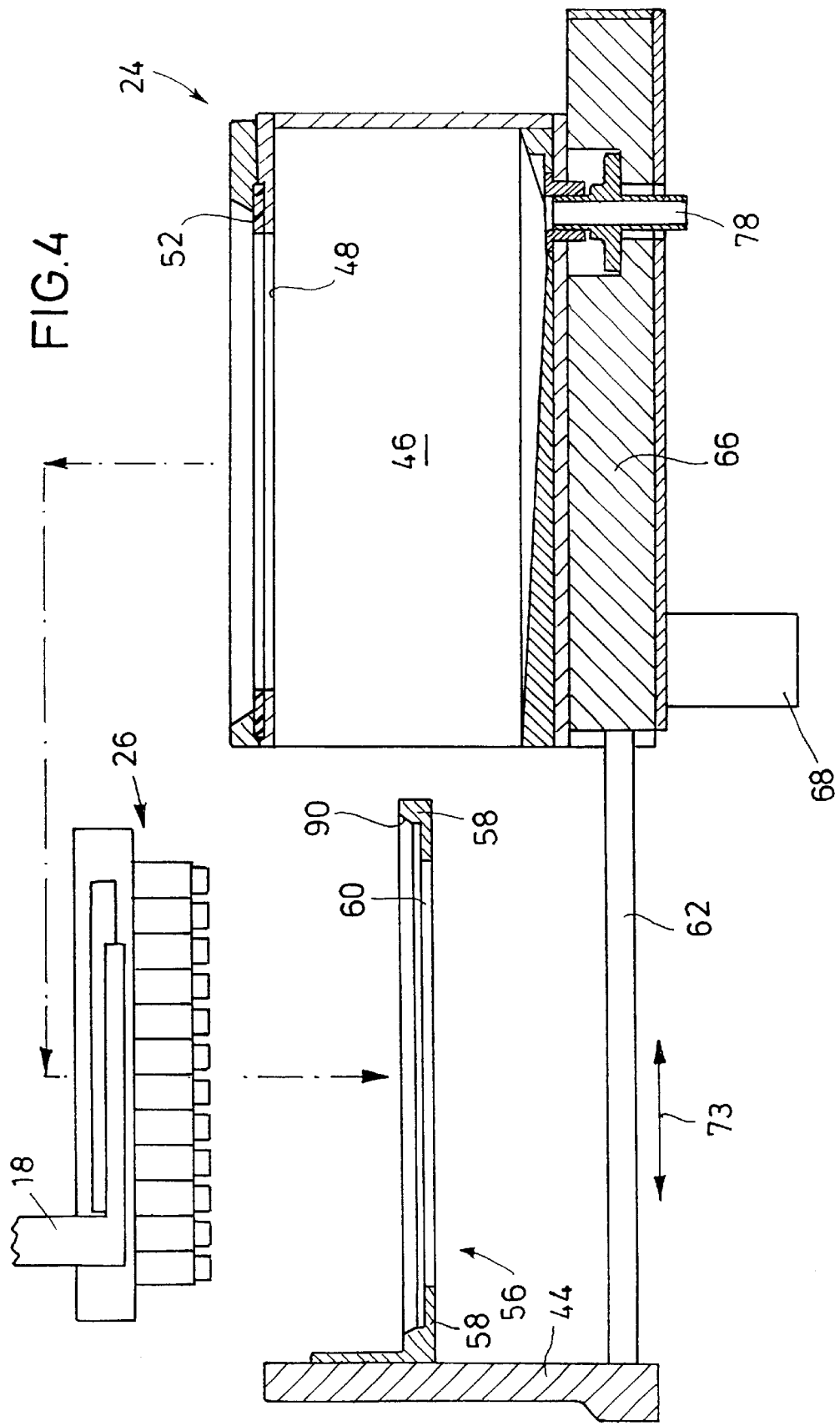
Figure 5:
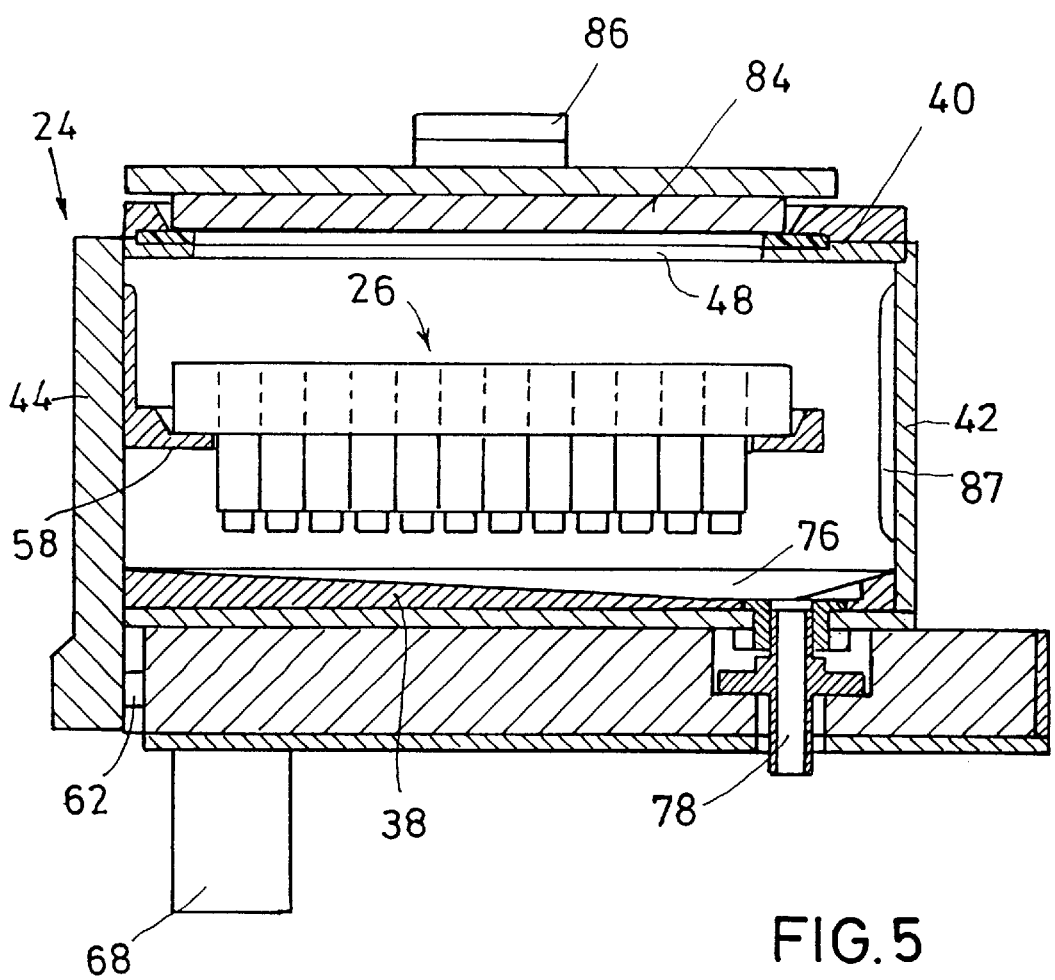

The invention will now be described in further details with reference to the drawing, in which:

FIG. 1 shows a lateral view of a pipetting machine with a gripping arm and a low pressure chamber, FIG. 2 shows a longitudinal section through the low pressure chamber in the closed state and with the carrier body being placed on top, FIG. 3 shows a section along line III—III of FIG. 2, FIG. 4 shows a longitudinal section through the low pressure chamber in the opened state to show the introduction of the carrier body into the low pressure chamber, and FIG. 5 shows a longitudinal section through the low pressure chamber in the closed state with the opening in the top wall being closed and the carrier body being located in the interior of the low pressure chamber for vacuum drying.

FIG. 1 shows, strongly schematized, a pipetting robot 10 comprising a movable bracket 12. The bracket 12 is movable along the rail 14 and comprises one or multiple pipetting needles 16 as well as a gripping device 18 with two gripping arms 20. The pipetting needles 16 and the gripping device 18 are movable along the bracket 12, thus being able to move in the X and Y directions relative to the table 22 of the machine 10.

Various utensils and objects required for the pipetting process are located on the table 22, which are not elaborated on for reasons of simplicity. Among other things, a low pressure chamber 24 is located on the table 22 which can be employed both for filtering under reduced pressure and for vacuum drying remaining liquid which might still be adhering to the carrier bodies 26 after a filtering process.

The construction of the low pressure chamber 24 and the carrier body 26 will subsequently be described with reference to FIGS. 1 to 5. As can be seen in FIG. 2, the carrier body 26 comprises a plurality of tubular compartments 28 each comprising an inlet opening 30 and an outlet opening 32. Filter bodies 34 in the form of porous matrix materials, frits or membranes are located in the compartments 28. The carrier body 26 comprises a rim 36 extending circumferentially laterally over the arrangement of the compartments 28.

The chamber 24 comprises a bottom wall 38 and a top wall 40 parallel thereto which are interconnected via four lateral walls 42, 44, three lateral walls of which (designated by 42 in the figures) are formed to be fixed and the fourth lateral wall 44 is formed movably to enable access to the interior space 46 of the chamber 24 (subsequently called access lateral wall). An opening 48 is located in the top wall 40, the opening edge 50 thereof comprising a sealing surface 52. Above the sealing surface 52, the opening edge 50 comprises an expanding centering zone 54.

The access lateral wall 44 is provided with a support mounting 56 comprising a circumferential frame 58 defining an insertion opening 60 and being fixedly connected from the inside to the access lateral wall 44. The frame 58 is arranged parallelly to the top wall 40 and the bottom wall 38. As can be seen especially in the case of FIGS. 3 and 4, two cam elements 62 project from the access lateral wall 44 which are guided axially displaceably in guiding rails 64 located in a base plate 66 supporting the bottom wall 38. A driving motor 68 is flanged on the plate 66 comprising a driving element 70 in the form of a cog wheel combing with a rack 72 connected to one of the two cam elements 62. In this manner, the access lateral wall 44 can be moved in the direction of the arrows 73 by means of the fixed lateral walls 42 or can be moved towards them. On the interior side of the access lateral wall 44, a circumferential seal 74 is located abutting on the fixed lateral walls 42, the top and the bottom walls 40, 38 and seals the interior space 46 of the chamber 24.

As can further be seen in the figures, the bottom wall 38 comprises an inclination 76 towards a drain pipe 78 to direct the liquid to a reception container 80. A vacuum pump 82 is connected to the drain pipe 78 via a suction conduit 81, through which pump air is drawn out of the interior space 46 to produce a low pressure. As can be seen in FIG. 5, the opening 48 in the top wall 40 of the chamber 24 can be closed by means of a lid 84 comprising a projection 86 for gripping the lid 84 by means of the gripping device 18 of the pipetting machine 10. Apart from the pressure, the temperature 46 of the chamber 24 can also be set, with at least one of the fixed lateral walls 42 being provided with one or multiple heating elements 87.

Subsequently, the operation and the use of the chamber 24 by means of the pipetting machine 10 will be elaborated on.

For the liquids present in the compartments 28 of the carrier body 26 to pass through the filter bodies 34, the carrier body 26 is inserted into the opening 48 of the top wall 40 of the chamber 24, the projecting rim 36 being placed on the sealing surface 52. The carrier body 26 is inserted into the opening 48 by means of the gripping device 18, with the carrier body 26 being centered in the opening 48 by the inlet zone 54 of the opening edge 50. During this procedure, the access lateral wall 44 is closed, with no carrier body 26 being located in the insert opening 60 of the support mounting frame 58. Then a first low pressure is produced in the interior space 46 of the chamber 24 due to which the liquids flow through the filter bodies 34. In this process, the low pressure amounts to about 400 to 800 mbar. During this phase, the heating elements 87 can be operated to pre-heat the interior space 46 of the chamber 24. The liquid flowing out of the outlet openings 32 of the compartments 28 gets into the reception container 80 via the drain pipe 78. The liquid can therefore be disposed of by other means, as the substance remaining in the filter bodies 34 is of interest for the analysis.

To make this substance of interest available for analysis, it has to be released from the filters 34. For this purpose, the carrier body 26 has to be placed onto a mounting 88 with a plurality of individual reception containers 90 in which the substances being released from the individual filter bodies 34 are received (see FIG. 1). As the quantities of the substances to be analyzed, respectively the components of the liquids, are rather small, and for the analysis to be performed correctly, it has to be provided that only the components to be analyzed get into the reception containers 90. Liquid drops which might still be adhering to the outlet openings 32 from the preceding filtering step can adulterate the measuring results, which is why they have to be removed before the elution process. For this purpose, the carrier body 26 located in the opening 48 of the top wall 40 is elevated by means of the gripping device 18 to introduce the carrier body 26 from the top into the insertion opening 60 of the frame 58. For this purpose, the motor 68 is actuated to move out the access lateral wall 44 until the frame 58 is completely moved out of the interior space 46 of the chamber 24. This situation is shown in FIG. 4, by means of which it becomes clear how the carrier body 26 is now inserted in the insertion opening 60 from the top, the edge thereof, like the opening edge 50, comprising an inlet zone 92. In this process, the control of the gripping device 18 can be selected such that the carrier body 26 is dropped shortly after being elevated and moved out of the opening 48 so that liquid drops which might still be adhering to the outlet openings 32 are released by the vibrations resulting therefrom. After the insertion of the carrier body 26 into the frame 58, the access lateral wall 44 is moved back towards the fixed lateral walls 42. Additionally, the gripping device 18 grips the lid 84 to close the opening in the top wall 40 with it.

Then the interior space 46 now substantially gastightly sealed is exposed to a low pressure which is substantially greater than the low pressure to draw the liquid through the filter body 34. The low pressure now establishing amounts to about 50 to 100 mbar. Additionally, a temperature range between 40 and 60 °C. is set by correspondingly controlling the heating elements 87 in the interior space 46. That way, the evaporation point of the liquid which might still be adhering to the outlet openings 32 is shifted, the liquid thus evaporating. After this vacuum drying process, the chamber 24 is re-aerated, and the access lateral wall 44 is moved so that the carrier body 26 liberated from liquid drops on the outlet openings 32 can be moved onto the mounting 88 for applying the elution buffer. Then the carrier body 26 is moved onto the opening 48 of the top wall 40 of the chamber 24. A carrier body with compartments is inserted into the frame 58, in which compartments the eluate of the compartments of the carrier body 26 is received, when it is drawn out therefrom by means of low pressure.

What is claimed is:
1. Device for selectively filtering liquid samples in compartments comprising inlet and outlet openings of a carrier body under reduced pressure and for vacuum drying drops of the sample liquid present in the area of the outlet openings of the compartments, comprising

- a chamber (24) comprising an interior space (46) limited by a top wall (40), a bottom wall (38) and lateral walls (42, 44) connecting them,
- the top wall (40) comprising an opening (48) with an opening edge (52) whereon a closing lid (84) or the carrier body (26) can selectively be placed in a substantially gastight manner by means of outlet openings (32) directed towards the interior space (46) of the chamber (24),
- one of the lateral walls being formed as an access lateral wall (44) which can be opened and closed substantially gastightly for introducing the carrier body (26) into the interior space (46) of the chamber (24), and
- the bottom wall (38) comprising a drain (76, 78) for liquid exiting from the outlet openings (32) of the compartments (28) of the carrier body (26), and
- a vacuum pump (82) with a suction conduit (81) terminating in the interior space (46) of the chamber (24) for producing a first low pressure for drawing liquid samples through the outlet openings (32) of the compartments (28) with the carrier body (26) being placed on the opening edge (50) of the top wall (40) and the access lateral wall (44) of the chamber (24) being closed and for producing a second low pressure higher than the first low pressure for drying drops of liquid samples still present on the outlet openings (32) of the compartments (28) with the carrier body (26) being located in the interior space (48) of the chamber (24) and the lid (84) being placed on the opening edge (50) of the top wall (40) as well as the access lateral wall (44) of the chamber (24) being closed.

2. Device according to claim 1, characterized in that a support mounting (52) is provided for receiving the carrier body (26) for locating it in the interior space (46) of the chamber (24).

3. Device according to claim 2, characterized in that the support mounting (56) is connected to the interior side of the access lateral wall (44) which is directed towards the interior space (46) of the chamber (24) and projects therefrom directing towards the interior space (46) of the chamber (24).

4. Device according to claim 1, characterized in that the access lateral wall (44) comprises at least one cam element (62) extending parallelly to the bottom wall (38) of the chamber (24), which element is guided in a guiding device (64) in the two opposite directions (73) of the extension thereof and that a driving means (68) is provided comprising a driving element (70) moving the cam element (62) towards the chamber (24) to move the access lateral wall (44) into substantially gastight abutment with the adjacent top, bottom and lateral walls (38, 40, 42) and moving the cam element (62) away from the chamber (24) to move the access lateral wall (44) from the chamber (24) to allow access to the interior space thereof.

5. Device according to claim 4, characterized in that the access lateral wall (44) or the adjacent top, bottom and lateral walls (38, 40, 42) of the chamber (24) comprises or comprise a seal (74).

6. Device according to claims 1, characterized in that at least one heating element (87) is provided for heating the interior space (46) of the chamber (24).

7. Device according to claim 6, characterized in that the heating element (87) is arranged on the interior side of at least one of the lateral walls (38, 40, 42, 44) which is directed towards the interior space (46) of the chamber (24).

8. Device according to claim 1, characterized in that the opening edge (50) of the top wall (40) of the chamber (24) comprises a support surface (52) for the lid (84) and the carrier body (26), which surface is arranged in the plane of the opening (48) or parallel thereto, and a conical insertion surface (54) extending angularly to the support surface (52) for centering the lid (84) and the carrier body (26) when they are being placed on the support surface (52).

9. Device according to claim 8, characterized in that the support surface (52) comprises a seal.

10. Device according to claim 1, characterized in that the suction conduit (81) connected to the vacuum pump (82) terminates in the drain (76, 78) of the bottom wall (38).

11. Device according to claim 1, characterized in that the closure lid (84) comprises a plate to be placed tightly on the opening (48) of the top wall (40).

12. Device according to claim 1, characterized in that the closure lid comprises a substantially gastight sealing body which can be placed onto the carrier body for substantially gastightly sealing the inlet openings of the compartments thereof.

13. Device according to claim 1, further comprising:
- a movable gripping device (18) for gripping the carrier body (26) comprising multiple compartments for receiving the liquid samples, and
- a control means for controlling the gripping device (18).

* * * * *